United States Patent [19]
Karwoski

[11] Patent Number: 4,797,094
[45] Date of Patent: Jan. 10, 1989

[54] ORTHODONTIC WIRE TERMINAL AND ATTACHMENT TOOL THEREFOR

[76] Inventor: Thaddeus M. Karwoski, 5420-B Roundtree Ct., Concord, Calif. 94521

[21] Appl. No.: 129,480

[22] Filed: Dec. 7, 1987

[51] Int. Cl.⁴ ............................................. A61Q 7/00
[52] U.S. Cl. ...................................................... 433/22
[58] Field of Search ...................... 433/2, 3, 4, 22, 17

[56] References Cited
U.S. PATENT DOCUMENTS
2,959,856 11/1960 Gurin ..................................... 433/22
3,683,502 8/1972 Wallsheim ............................. 433/22

FOREIGN PATENT DOCUMENTS
3149544 7/1983 Fed. Rep. of Germany .......... 433/2

Primary Examiner—Robert Peshock
Attorney, Agent, or Firm—Linval B. Castle

[57] ABSTRACT

A rounder terminal cap is fitted to the end of an orthodontic wire to reduce cheek injury from the sharp wires and is secured by a very small set screw in the cap. The set screw is tightened by a novel tool having a rotatable set screw wrench at the end of a bevel geared rotatable shaft in a elongated housing. For installation, the tool captures a cap between a slideable box or plate that secures a cap on its set screw until the cap is placed on an orthodontic wire and the set screw tightened. The slideable box is then moved to release the cap from the tool.

8 Claims, 1 Drawing Sheet

U.S. Patent  Jan. 10, 1989  4,797,094

ORTHODONTIC WIRE TERMINAL AND ATTACHMENT TOOL THEREFOR

CROSS REFERENCE TO RELATED APPLICATIONS

The invention disclosed herein is also disclosed in my pending Design patent applications, Ser. No. 06/857,469, filed Apr. 29, 1986, (now abandoned) and Ser. No. 07/073,423, filed July 15, 1987.

BRIEF SUMMARY OF THE INVENTION

This invention relates to orthodontal apparatus and in particular to a novel orthodontic wire terminal cap and the tool for attachment and removal of the terminal cap.

For both cosmetic or medical purposes, a large percentage of today's youth are requiring orthodontic treatment including the fastening of tight metal bands or wires to the teeth to force them into a desired form. The wires usually are fastened to the exterior surface of each tooth and extend around the jaw to their ends near the rear molars and in an area of the mouth where the inner cheek normally contacts those teeth.

Orthodontic wires are relatively small in diameter and their ends are sharp enough to puncture the delicate inner cheek tissues of many patients. It is therefore one object of this invention to provide a small rounded terminal cap which may be secured to the sharp ends of the orthodontic wires to thereby prevent such wire punctures and eliminate the pain resulting therefrom.

As a patient's teeth adjust to the pressures of the tight orthodontic wires, it becomes necessary to adjust and usually shorten the wires. This requires the removal of a wire terminal cap, a cutting of the wire, and a reinstallation of the cap. Thus, a terminal cap must necessarily have some means for tightening it on a wire and subsequently loosening it for removal, to be followed again by reinstallation and tightening. Accordingly, the terminal cap to be disclosed not only has an axial hole for inserting the orthodontic wire end, but also a very small threaded radial hole that intercepts the axial hole and which contains a small socket head set screw for securing the terminal cap to the wire.

Because a terminal cap is normally located near the rear molar, it would be virtually impossible for an orthodontist to attach such a terminal cap to an orthodontic wire attached to a patient's teeth by using a very small but conventional Allen or similar type of socket wrench.

Therefore, the invention disclosed herein includes a long, thin attachment wrench that holds a terminal cap before and while being mounted to a wire and which may used to conveniently and rapidly tighten or loosen the set screw in the cap.

BRIEF DESCRIPTION OF THE DRAWINGS

In the drawings which illustrate the preferred embodiment of the invention.

DETAILED DESCRIPTION

Figure 1:
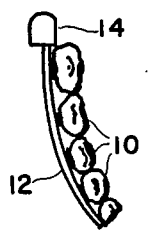
FIG. 1 is a partial plan view of an orthodontic wire with a terminal cap installed.

Illustrated in FIG. 1 is a plan view representing a portion of a jaw showing several teeth 10 banded by an orthodontic wire 12. To prevent the sharp end of the wire 12 from gouging into the tender inner cheek tissues of the patient, a terminal cap 14 has been attached. The cap 14 is smooth with rounded edges. It may be formed from a suitable plastic material but is preferably formed of a non-corrosive stainless metal which can be drilled and threaded to accept a set screw as illustrated in FIG. 2.

Figure 2:
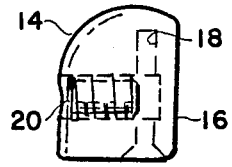
FIG. 2 is a sectional side elevational view of a terminal cap.

FIG. 2 is a greatly enlarged sectional side elevational view of the terminal cap 14 illustrating one preferred form of the cap. So that the cap and orthodontic wire may closely lie against the teeth of the patient, a flat surface 16 parallel with the longitudinal axis of the dome shaped cap is provided. A small hole 18 parallel with the axis and the surface 16 is drilled to accommodate the end of a orthodontic wire, and a radial hole 20 is bored and threaded to receive a very small socket head set screw which will secure the cap 14 to the orthodontic wire when tightened.

Figure 3:
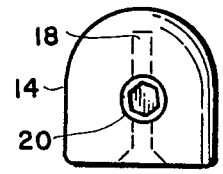
FIG. 3 is a sectional front elevation view of the cap of FIG. 2.
Figure 4:
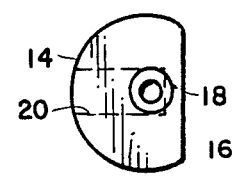
FIG. 4 is a sectional bottom plan view of the cap of FIG. 2.

FIG. 3 is another elevational side view of the orthodontal wire terminal cap 14 illustrating a set screw in the radial hole 20 and the hole alignment with the center of the axial wire hole 18. FIG. 4 is a bottom plan view of the terminal cap 14 illustrating the wire hole 18.

Figure 5:
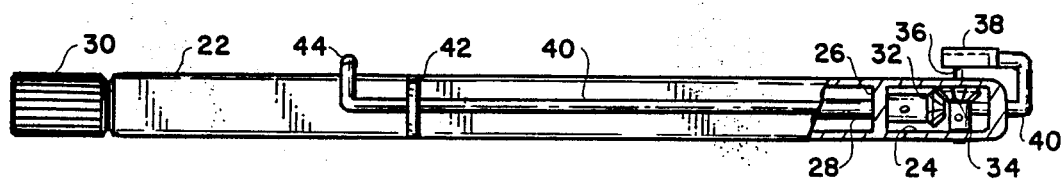
FIG. 5 is a side view, partially in section, of the orthodontic wire terminal cap attachment wrench.
Figure 6:
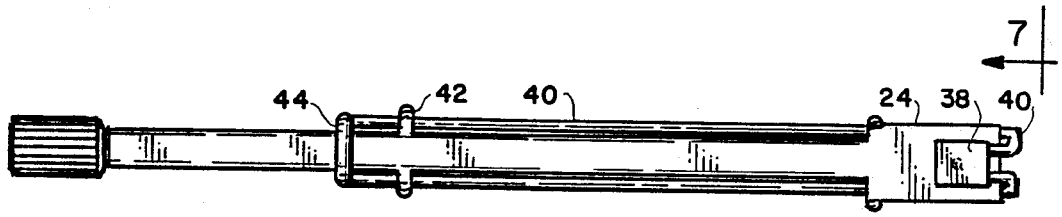
FIG. 6 is a top plan view thereof.
Figure 7:
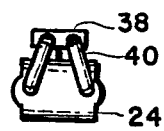
FIG. 7 is an end view taken along the lines 7—7 of FIG. 6.

FIG. 5 is a side elevational view of an attachment tool into which a terminal cap 14 may be mounted and which is to be used to place and tighten the cap on the end of an orthodontic wire in a patient's mouth. Because the tool is to be used in the area of the rear molar teeth, it should be approximately six inches long and must be thin so that it may be readily and painlessly positioned between the jaw and inner cheek.

The attachment tool comprises a tubular housing 22 closed at a first end and terminating at its second end in a bevel gear box 24 which is separated from the main part of the housing by a partition 26. Extending longitudinally through the housing 22 and partition 26 is a rotatable shaft 28 which is coupled at the first end of the housing to a rotatable knob 30. The shaft 28 extends through the partition 26 into the gear box 24 where it is connected to a first bevel gear 32 that engages a second preferably identical bevel gear 34 mounted on a short shaft at right angles to the rotatable shaft 28 and journalled for rotation in the top and bottom walls of the gear box 24. Attached to one end of the short shaft on the gear 34 is a very small straight section of an Allen wrench 36. Thus, rotation of the rotatable knob 30 will rotate the Allen wrench 36.

A terminal cap is held by the attachment tool while installing and removing the cap from an orthodontic wire by a longitudinally movable box 38 having an open first end. The box 38 is adjustable between a position directly overlying the Allen wrench 36 and a position approximately a quarter inch behind that point. The box 38 is moved by a pair of rods 40 which are attached to the second end of the box adjacent the second end of the housing gear box 24, are bent down and reversed to slideably pass through guide holes through the edges of the gear box 24 toward the first end of the housing, and thence they slideably extend through guide tabs 42 in the sides of the housing to a point of rod connection 44 about a half inch behind the tabs and toward the first end of the housing. Thus, the box 38 may be moved from its position over the Allen wrench rearward away from the wrench by movement of the rod 40 from a position near the rotatable knob 30 at the first end of the housing.

As best shown in FIG. 5, the box 36 has side walls, a rear wall, and a thin top wall, and is open on the bottom side adjacent the Allen wrench and the first end facing the first end of the housing. To install an orthodontic wire terminal cap, such as the cap 14 of FIGS. 1-4, on a wire in a patient's mouth, the rod 40 is first moved to position the box 36 away from the Allen wrench. The terminal cap 14 Allen screw is then fitted to the Allen wrench on the attachment tool with the flat side surface 16 of the cap positioned to face the thin top wall of the box 38 and the axial hole 18 in the cap facing toward the first end of the tool housing and in view of the orthodontist. The rod 40 is then withdrawn to thus lock the terminal cap between the box top wall and Allen wrench and the terminal cap, still captured in the attachment tool, is fitted over the end of the orthodontic wire. Rotation of the knob 30 in the appropriate direction will then tighten the Allen socket screw in the threaded hole 20 to secure the cap 14 to the end of the orthodontic wire. When secured, the rod 40 and box 38 is again moved to release the cap 14 from the tool and the tool is lifted from its engagement with the Allen wrench and removed.

The removal of a terminal cap from an orthodontic wire is similarly simple and merely involved the reverse operation.

Having thus described my invention, what I claim is:

1. A terminal cap for reducing injury to a patient from the sharp ends of orthodontic wires, said terminal cap comprising:
    a small domelike body having a first hole therethrough for accommodating the end of the orthodontic wire, and
    A set screw threaded into a secod hole substantially normal to and intercepting said first hole in said body, said set screw for removably securing said body to said orthodontic wire.

2. The terminal cap claimed in claim 2 wherein said cap has a planar surface substantially parallel with said first hole and opposite said second hole.

3. In combination with a orthodontic wire terminal cap having a first hole for receiving the end of an orthodontic wire and a threaded second hole perpendicular to and intersecting said said first hole and containing a threaded set screw, a terminal cap attachment and removal tool comprising:
    an elongated rotatable shaft having first and second ends;
    rotating means on the first end of said shaft for rotating said shaft;
    set screw engaging means adjacent the second end of said shaft and rotatable about an axis substantially perpendicular to the longitudinal axis of said shaft in response to rotation of the shaft; and
    terminal cap capture means coupled to said tool and controlled from a position near the first end of said shaft for selectively holding and releasing a terminal cap having its threaded set screw engaged with said set screw engaging means.

4. The tool claimed in claim 3 wherein said screw engaging means includes a set screw engaging shaft on a first bevel gear engaging and rotatable by a second bevel gear on said elongated rotatable shaft.

5. The tool claimed in claim 4 wherein said terminal capture means includes a longitudinally movable box member overlying the end of said set screw engaging shaft, said box member being open on its side adjacent said set screw engaging shaft and on the end toward said rotating means.

6. The tool claimed in claim 5 wherein said box member is longitudinally movable from a position overlying the end of said set screw engaging shaft to position distal of said rotating means by a box moving rod extending from said box member to a location near said rotating means.

7. The tool claim in claim 6 wherein said box moving rod is slidable along a path parallel with said rotatable shaft.

8. An orthodontic appliance tool for positioning and securing a terminal cap to the end of an orthodontic wire, said terminal cap being secured by the tightening of a radial set screw in said cap against the orthodontic wire in an axial hole in said cap, said tool comprising:
    a thin elongated tubular housing having first and second ends;
    a rotatable shaft extending through said housing, said shaft terminating in a rotating knob at the first end of said housing and within a gear box formed at the second end of said housing, said housing having at least a top wall;
    a first bevel gear within said gear box and coupled to the end of said rotatable shaft for rotation therewith;
    a second bevel gear within said gear box connected to a set screw engaging shaft substantially perpendicular to said rotatable shaft, the end of said set screw engaging shaft extending through a top wall of said gear box, said second bevel gear engaging said first bevel gear for rotation therewith;
    a terminal cap positioning member overlying said gear top wall and the end of said set screw engaging shaft, said member having a surface substantially parallel with the top wall of said gear box for capturing an orthodontic wire terminal cap engaged on said set screw engaging shaft between said member and said gear box top wall; and
    a slide rod having a first end coupled to said terminal cap positioning member and a second end at a location near the rotating knob on said rotatable shaft, said slide rod being slideable through tabs extending from said tubular housing for moving said positioning member to release and recapture a terminal cap.

* * * * *